United States Patent
Alothmany et al.

(10) Patent No.: US 11,305,152 B2
(45) Date of Patent: Apr. 19, 2022

(54) APPARATUS FOR HUMAN GAIT MANIPULATION

(71) Applicant: King Abdulaziz University, Jeddah (SA)

(72) Inventors: Nazeeh Alothmany, Jeddah (SA); Ehab Hafiz Wali, Jeddah (SA); Abdulhameed Alkhateeb, Jeddah (SA); Umar Alabasi, Jeddah (SA); Mirza Pasovic, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/354,192

(22) Filed: Jun. 22, 2021

(65) Prior Publication Data
US 2021/0308520 A1     Oct. 7, 2021

Related U.S. Application Data

(63) Continuation of application No. 16/822,335, filed on Mar. 18, 2020.

(51) Int. Cl.
*A63B 22/02*     (2006.01)
*A63B 5/22*      (2006.01)
(Continued)

(52) U.S. Cl.
CPC ........ *A63B 22/0285* (2013.01); *A61B 5/1038* (2013.01); *A61B 5/6807* (2013.01);
(Continued)

(58) Field of Classification Search
CPC ...... A63B 22/0285; A63B 22/02–0292; A63B 2022/0092–0094; A63B 2244/088
See application file for complete search history.

(56) References Cited

U.S. PATENT DOCUMENTS 9,039,579 B1 * 5/2015 Osime .................. A61H 39/04
                                                          482/54
10,010,748 B1 * 7/2018 Weinstein ............ A63B 22/02
(Continued)

FOREIGN PATENT DOCUMENTS

CN     104545813 B     8/2016
CN     110124263 A  *  8/2019
(Continued)

OTHER PUBLICATIONS

Sandra Keller Chandra, et al., "Gaze strategies for avoiding obstacles: differences between young and elderly subjects", Gait & Posture, https://www.zora.uzh.ch/id/eprint/48651/7/Keller_Chandra_etal_Gait+Posture_2011_post-print.pdf, Jul. 2011, 24 pages.

*Primary Examiner* — Joshua Lee
*Assistant Examiner* — Kathleen M Fisk
(74) *Attorney, Agent, or Firm* — Oblon, McClelland, Maier & Neustadt, L.L.P.

(57) ABSTRACT

A treadmill may be configured for gait training and/or therapy with attachable/detachable barriers affixable to a belt and/or with a vertical obstacle module and/or with sensor systems, but without requiring hoists, harnesses, attachments to the treadmill or base, or frame, and/or excessively high treadmill frames, such as those that exceed the height of the person on the treadmill. The barriers on the belt are configured to modify movement of only one foot of a person on the treadmill. The treadmill may use a single, integral belt. Methods of gait training and/or therapy may involve such treadmills without excessive expense and without excessive modification of standard treadmill equipment.

8 Claims, 13 Drawing Sheets

(51) Int. Cl.
*A63B 22/00* (2006.01)
*A63B 21/00* (2006.01)
*A63B 24/00* (2006.01)
*A61B 5/00* (2006.01)
*A61B 5/103* (2006.01)

(52) U.S. Cl.
CPC .......... *A63B 5/22* (2013.01); *A63B 21/00192* (2013.01); *A63B 22/02* (2013.01); *A63B 24/0062* (2013.01); *A63B 2022/0092* (2013.01); *A63B 2022/0094* (2013.01); *A63B 2024/0093* (2013.01); *A63B 2220/833* (2013.01)

(56) References Cited

U.S. PATENT DOCUMENTS

2004/0192511 A1* 9/2004 Ein-Gal ................ A61H 7/001 482/54
2006/0247104 A1 11/2006 Grabiner et al.
2017/0027803 A1 2/2017 Agrawal
2018/0345070 A1 12/2018 Yakovenko et al.

FOREIGN PATENT DOCUMENTS

| DE | 202011100239 U1 * | 8/2012 | ......... A63B 22/0285 |
|---|---|---|---|
| GB | 2 291 361 A | 1/1996 | |
| JP | 2019-71986 A | 5/2019 | |
| WO | WO 2013/054257 A1 | 4/2013 | |

* cited by examiner

APPARATUS FOR HUMAN GAIT MANIPULATION

CROSS-REFERENCE TO RELATED APPLICATIONS

The present application is a Continuation of U.S. application Ser. No. 16/822,335, pending, having a filing date of Mar. 18, 2020.

BACKGROUND OF THE INVENTION

Field of the Invention

The present disclosure relates to therapeutic and/or training equipment, particularly moving bands, such as treadmills, which may have barriers and/or obstacles arranged on, upon, around, and/or above the belt so as to modify the gait, including aspects such as foot orientation, pace, rhythm, and/or coordination, as well as to methods of gait therapy and/or training or methods of making devices for such therapy and/or training.

Description of the Related Art

Many living beings and human health care patients, suffer from mobility limitations, including asymmetry in walking patterns due to neuro-motor and/or musculoskeletal impairments. Such impairments may reduce the ability to walk and may even cause skeletal deformities. Consequently, such mobility impairments can affect the performance of daily living activities, increase the risk of fall, and negatively impact quality of life.

There are different medical conditions that can result in asymmetric gait patterns and motor impairment in humans, such as stroke in adults and cerebral palsy in children and adults. Stroke is the leading cause of disability and the fifth cause of death in the US. Affected individuals can suffer from severe neuro-motor impairments that affect normal walking and increase dependence on the unaffected side for daily living activities. Specifically, walking velocity, cadence, and/or step length, i.e., gait cycle parameters, can be considerably altered after strokes. These altered gait cycle parameters are associated with higher risk of falls and more dependent lifestyles.

There are a number of different approaches to correcting and/or reducing walking asymmetry and improving rhythm in affected individuals. One corrective approach is the traditional rehabilitation approach, i.e., task-oriented training, which instructs the patient verbally to adjust the walking pattern and/or rhythm based on gait parameters, while performing a repeated functional tasked exercise. A second corrective approach involves using an auditory feedback system, such as the METRONOM system, wherein the patient tries to walk several steps while following a predefined tone or sound. A third approach involves using a split treadmill that has a separate engine for each belt, which allows for altering gait parameters for both limbs simultaneously, thereby improving gait pattern and asymmetry.

Most of the current therapeutic approaches to improve walking asymmetry mainly target an affected limb. Selected approaches in the art, such as those in US 2017/0027803 A1, WO2013054257A1, and US20060247104A1, aim to remedy walking asymmetry using a treadmill using an exoskeleton, cable attachments, and/or virtual reality applications to improve walking, which adds extra weight to the affected limb and complexity.

US 2017/0027803 A1 by Agrawal et al. (Agrawal) discloses systems for machine-based rehabilitation of movement disorders including gait therapy applications that can apply controlled forces to the pelvis and/or other body parts including knee and ankle joints. Agrawal describes cable-driven systems for gait therapy applications applying controlled forces to the pelvis and the pelvis, knee, and ankle joints, which can be treadmill or walker-based. Agrawal applies a controlled downforce to the hip with augmentation including supportive forces. Agrawal's technology may be activated through cables providing support and limb-flexing moments with low inertia and friction resistance, optionally by facilitating a patient's ability to coordinate movement, control balance, achieve strength, and other beneficial outcomes. Agrawal uses winches, systems of cables and leg attachments, load cells attached to the treadmill, and/or an exoskeleton.

WO 2013/054257 A1 by Mirelman et al. (Mirelman) discloses methods and/or systems for diagnosing, monitoring, and/or treating persons at risk for falling and/or other pathological conditions. Mirelman's system diagnoses people before they actually start falling, optionally including trying out and identifying one or more fall triggers using virtual reality tools. Mirelman's treatment may include training the persons using situations and/or triggers which are determined to be relevant for that person. Mirelman uses virtual reality simulation as well as body attachments.

US 2006/0247104 A1 by Grabiner et al. (Grabiner) discloses an apparatus, system, and method for fall prevention training that delivers, studies, and analyzes the biomechanics of a disturbance event, such as a slip or trip incident, so that an appropriate response can be executed by the person to reduce or eliminate the number of falls experienced. Grabiner's apparatus includes a platform that delivers a disturbance event in less than about 500 ms, preferably 100 to 200 ms. Grabiner also uses a harness system on at least the torso of the patient, tethers and force transducers, though Grabiner may use a physical obstacle on its treadmill. Grabiner requires a pair of belts, i.e., left and right belts, and describes only physical barriers which span the width of both of Grabiner's belts. Grabiner's barriers are not affixed to either belt.

GB 2 291 361 A by Omoyiola (Omoyiola) discloses an exercise treadmill with supporting surfaces made from a plurality of stretchable belts so arranged that a person using the treadmill may accelerate/decelerate smoothly to/from full speed because each succeeding sector of the belt surface is moving at a faster/slower rate. Omoyiola's treadmill may have fixed hurdles or hurdles that are synchronized with the belt movement. Omoyiola describes a number of mobile and/or immobile hurdles for a traditional treadmill, which hurdles may be the same as used by athletes. Omoyiola's hurdles may be powered by the same mechanism as the treadmill or a separate adjoining mechanism. Omoyiola's hurdle may have reducible heights and the movable hurdles are connected by a chain link (on rollers) on one or both sides of the treadmill, rather than the belt.

JP 2019-071986 A by Kogu et al. (Kogu) discloses a walking/gait training apparatus that has a physical obstacle and trains for fall prevention and improves cognitive function. Kogu's walking training apparatus includes a rotating body having a walking unit and a trip prevention unit that lifts the trainee before the trainee walking on the walking unit falls. Kogu's belt can have convex-shaped obstacles on its surface, and the system has a fall prevention unit including a column member, a beam member, a grip portion, a wire, and a mounting portion, which attach to the patient's waist. Kogu's obstacles may be various shapes and may be attachable and removable from holes in Kogu's belt.

CN 104545813 B by Ning et al. (Ning) discloses a traveling obstacle avoidance capacity testing device. Ning's device includes a photoelectric virtual obstacle generation device on a pressure detection step pad. A pressure scanning matrix device in Ning's pressure detection step pad is connected with a control device through a signal acquisition device. The photoelectric virtual obstacle generation device is connected with the control device. A computer is connected with the control device through a communication device. Ning's pressure detection step pad is formed by pressing and fixing a hard base pad, a pressure scanning matrix device, and a buffer soft pad. The photoelectric virtual obstacle generation device comprises LED light strips which are uniformly spaced from one another in parallel. Ning's device can establish a state of normal walking, directly measure gait parameters, and avoid fall risk in tested persons. Ning's obstacles are light, i.e., virtual obstacles.

*Gait & Posture* 2011, 34(3), 340-346 by Chandra et al. (Chandra) discloses an investigation of gaze-behavior in elderly, middle-aged, and young subjects walking on a treadmill repeatedly stepping over obstacles, which approached either on the right or left side. An acoustic warning signal announced the obstacles in Chandra, after which subjects were free to look wherever they wanted. Gaze-movements were measured by video-oculography. Chandra reports that gaze-behavior of elderly subjects indicate a greater dependency on visual inputs. Chandra does not describe barriers attached to the belt, nor removable barriers.

In light of the above, a need remains for therapeutic and/or training devices, including treadmills with simplified barrier systems, particularly for patients with impaired gaits and/or handicaps, such as stroke patients, and methods of making and using such devices.

SUMMARY OF THE INVENTION

Aspects of the invention provide treadmills configured for gait manipulation, such treadmills comprising: a treadmill belt configured to travel within a hollow treadmill frame upon rotating elements having axes perpendicular to a direction of the travel; a first barrier; and a second barrier; wherein the first and second barriers are arranged on the top surface of the treadmill belt between a first lengthwise edge and a second lengthwise edge of the treadmill belt, wherein the first and second barriers are reversibly fastened to the treadmill belt and are interchangeably positionable along the first lengthwise edge and the second lengthwise edge of the treadmill belt, wherein the barriers extend no more than 75% of a width between the first and second lengthwise edge, wherein the barriers on the belt are configured to modify movement of only one foot of a person on the treadmill, and wherein a distance between the first lengthwise edge and the second lengthwise edge of the treadmill belt defines the width of the treadmill belt. Such treadmills may be modified by any permutation of the features described herein, particularly the following.

Inventive treadmills may further comprise three or more barriers, wherein each of the obstacles is equidistantly positioned along a length of the treadmill belt.

The hollow frame need not exceed a height of the person, or chest height of the person, on the treadmill. The treadmills may be configured to have no physical connection between the person on the treadmill and the hollow frame and/or no physical connection between the person on the treadmill and the treadmill.

Inventive treadmills may further comprise an external mechanical obstacle module comprising an extendable/retractable rod-shaped obstacle, wherein the obstacle is configured to extend across at least a portion of the belt of the treadmill from the external mechanical obstacle module. The external mechanical obstacle module(s) may be positioned adjacent the treadmill belt such that the obstacle is extendable vertically above the belt. The obstacle may be configured to extend perpendicular to the first and second lengthwise edge of the belt. The obstacle may be configured to extend across no more than 60% of the width of the belt.

Inventive treadmills may further comprise: a set of frame magnetic coils, configured to create an electromagnetic field barrier generated from the set of magnetic coils; and a wearable magnet magnetically coupled with the set of frame magnetic coils, wherein the set of magnetic coils is integrated into a treadmill frame, wherein the wearable magnet is configured to be integrated into a shoe worn by the person on the treadmill, and wherein the set of frame magnetic coils and the at least one wearable magnet are operatively coupled with a microprocessor.

Inventive treadmills may further comprise: a foot sensor; a front stride sensor; and a rear stride sensor, wherein the foot sensor is configured to be integrated into a shoe worn by the person on the treadmill, wherein the front stride sensor and the rear stride sensor are positioned under the treadmill belt adjacent a bottom surface of the treadmill belt, wherein the foot sensor is communicably coupled with the front stride sensor and the rear stride sensor, wherein the foot sensor, the front stride sensor, and the rear stride sensor are operatively coupled with a microprocessor, a set of strike related information being transferred to the microprocessor from the sensors, and wherein the electromagnetic field is managed by the microprocessor according to the set of strike related information.

The first and second barrier may include a first belt side attachment and a second belt side attachment, and the treadmill may further comprise: a lengthwise treadmill wall positioned along the first lengthwise edge; and a center treadmill wall positioned parallel to the lengthwise treadmill wall and along a center of the treadmill belt, wherein the first belt side attachment is laterally connected to a shoe worn by the person on the treadmill, wherein the second belt side attachment is laterally connected to the shoe opposite the first lateral attachment, wherein the first belt side attachment is slidably positioned along the lengthwise treadmill wall using a first rotatable ball mount, and wherein the second belt side attachment is slidably positioned along the center treadmill wall using a second rotatable ball mount.

The first and second barrier may be in the form of triangular and/or rectangular prisms. The belt may comprise the barriers on only one half of the width of the belt from a center of the belt. The barriers may be driven only by the belt in operation. Each of the barriers may be mirror-symmetric in at least two planes bisecting the barrier. The barriers may be made of a material comprising a polyurethane foam.

Aspects of the invention provide methods of correcting a gait of a person, and such methods may comprise: conducting a physical therapy regime on ambulatory motion of the person using any permutation of the inventive treadmill described herein.

Aspects of the invention provide methods of conducting physical therapy on the gait of a person, and such methods may comprise: aligning the barriers of any permutation of the inventive treadmill described herein on only one lengthwise half of the belt in the direction of movement of the belt; and allowing the person to walk and/or run on the treadmill.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
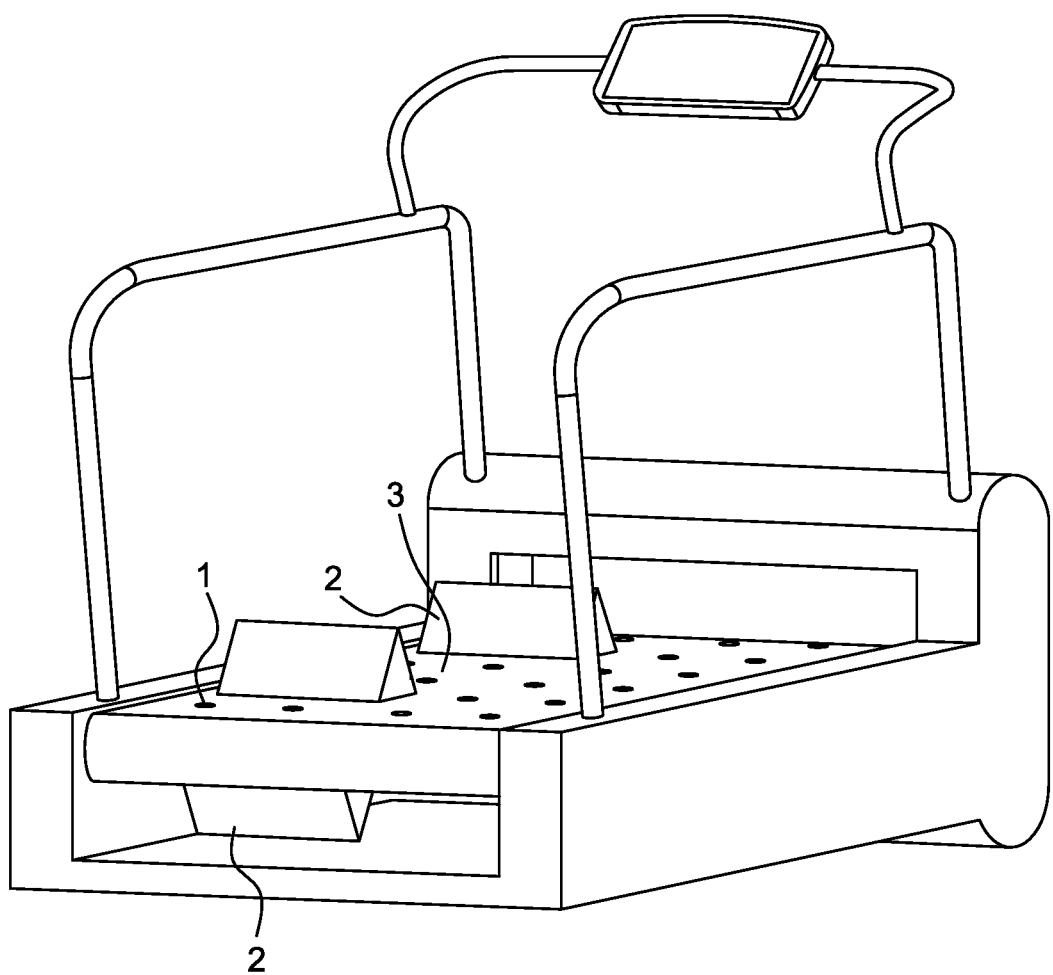
FIG. 1 shows a sketch of a treadmill equipped with a specialized belt within the scope of the invention.
Figure 2A:
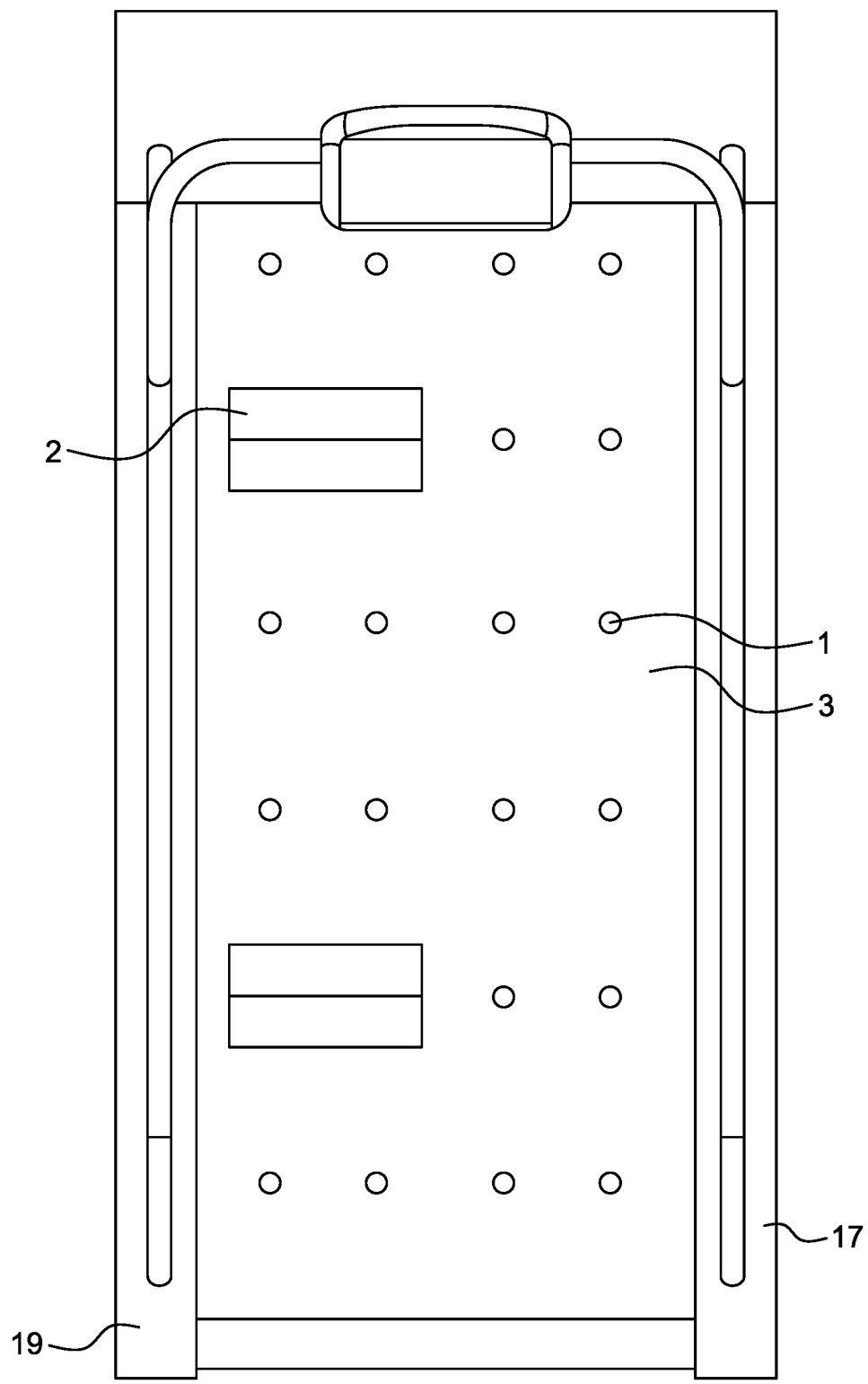
FIG. 2A shows a top plan view of an exemplary treadmill arrangement within the scope of the invention.
Figure 2B:
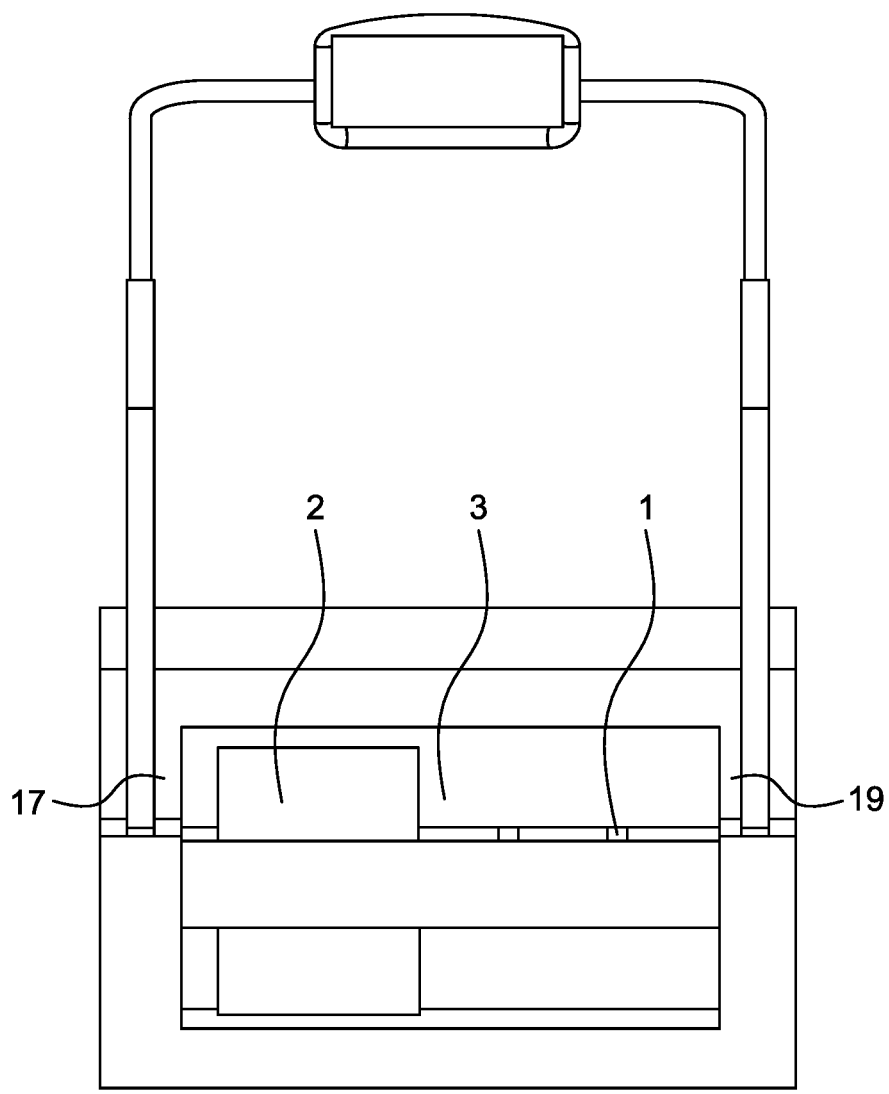
FIG. 2B shows a rear view of an exemplary treadmill arrangement within the scope of the invention.
Figure 2C:
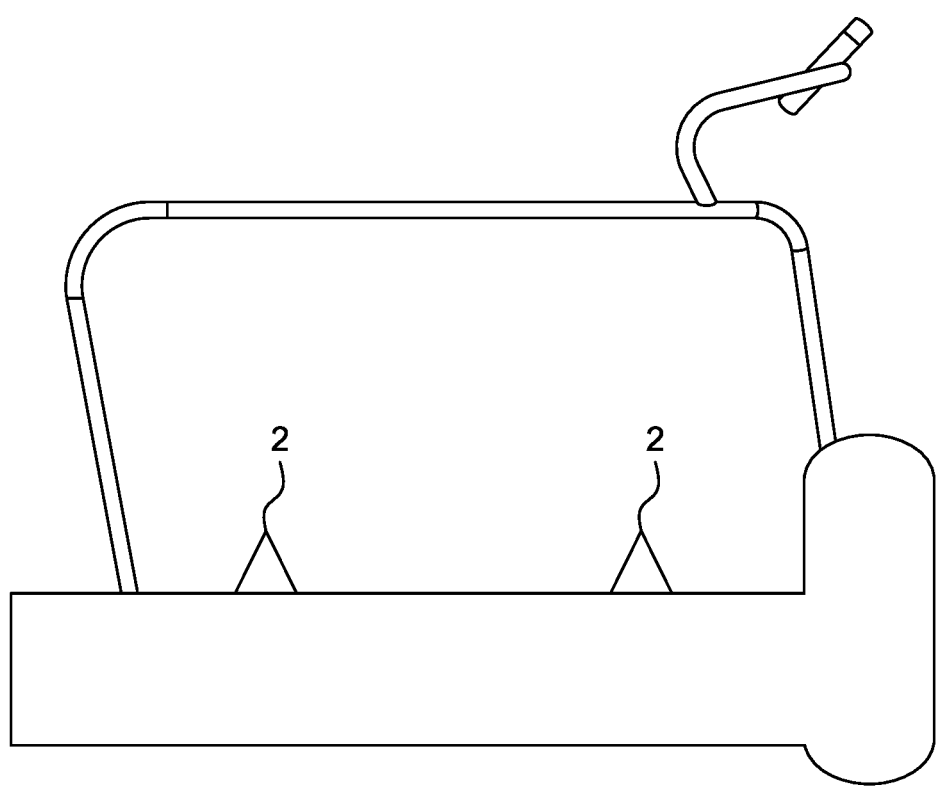
FIG. 2C shows a right side view of an exemplary treadmill arrangement within the scope of the invention.
Figure 2D:
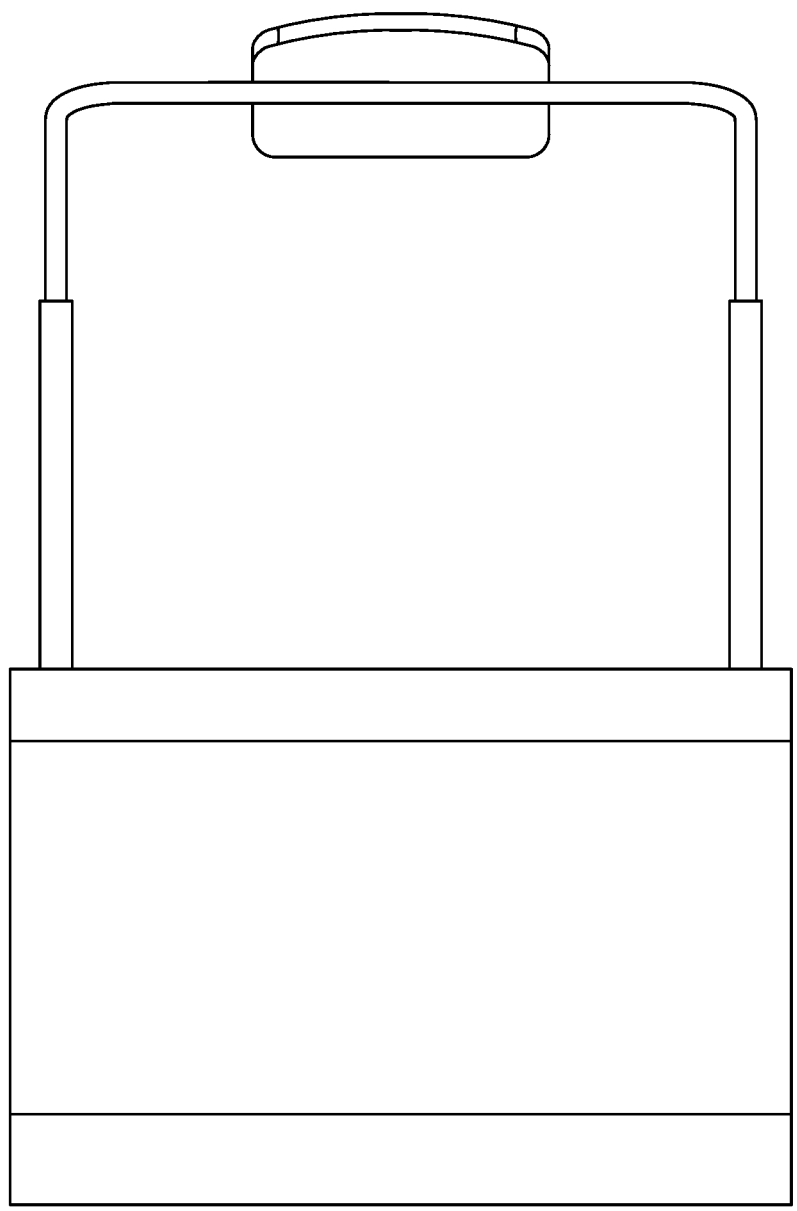
FIG. 2D shows a front view of an exemplary treadmill arrangement within the scope of the invention.

Aspects of the invention provide treadmills configured for gait manipulation (modification, improvement, therapy, or the like), such treadmills comprising: a treadmill belt (e.g., comprising rubber such as polybutadiene, olefin rubber, SBR, nitrile rubber, or the like, composite, and/or fibers) configured to travel spatially within a hollow treadmill frame (typically including an arm support on each side and a screen support in the front, these are optional features beyond the based/floor elements supporting the belt and rotating elements), upon rotating elements having axes perpendicular to a direction of the travel; a first barrier; and a second barrier. The first and second (and any further) barriers may be the same or different, in (repeat) patterns of shape, such as A-A-B-B-A-A, A-B-A . . . , A-B-C . . . , A-A-B-B-C-C . . . , etc., or the like. The first and second barriers may be arranged on, i.e., placed in contact with, attached to, or otherwise connected to, the top surface of the treadmill belt between a first lengthwise edge and a second lengthwise edge of the treadmill belt. The first and second barriers may be reversibly fastened, affixed, connected, attached, etc., to the treadmill belt and are interchangeably positionable along the first lengthwise (in direction of rotation of the belt) edge and the second lengthwise edge of the treadmill belt. The barriers may extend no more than 75, 67, 60, 50, 47.5, 45, 42.5, 40, 37.5, 35, or 33% (and at least 10, 15, 20, 25, 27.5, 30, 32.5, 35, or 40%) of the width between the first and second lengthwise edge, and/or the width of the belt. The distance between the first lengthwise edge and the second lengthwise edge of the treadmill belt defines the width of the treadmill belt. The barriers on the belt may be configured to modify movement of only one foot of a person on the treadmill, such that only one half of the belt contains such barriers.

Inventive treadmills may further comprise three (4, 5, 6, 7, 8, 9, 10, . . . ) or more barriers or may contain, e.g., no more than 1, 2, 3, 4, or 5 barriers/obstacles, and/or each of the barriers/obstacles is equidistantly positioned along a length of the treadmill belt. It is not necessary, and may even be desirable, however, that the barriers/obstacles are not equidistantly distributed, or are otherwise irregularly arranged.

The hollow frame need not and preferably may not exceed a height (e.g., top of the head) of the person, and/or breast, chest (rib cage), stomach, or waste height of the person on the treadmill. The treadmills may be configured to have no (though, in some circumstances, only one, two, or three) physical connections, such as cables, wires, harnesses, attachments, etc., between the person on the treadmill and the hollow frame and/or no such physical connection (in some circumstances, only one, two, or three) between the person on the treadmill and the treadmill (or any associated component in the room/space of the treadmill, particularly associated with the gait training).

Inventive treadmills may further comprise an external mechanical obstacle module comprising an extendable/retractable rod-shaped (cylindrical) obstacle or triangular, square, rectangular, or hexagonal prismatic obstacle, or 2, 3, 4, 5, or more such obstacles. Such obstacle(s) may be configured to extend across at least a portion of the treadmill belt, typically at least 10, 15, 20, 25, 30, 35, or 40% of the width and/or up to 75, 70, 65, 60, 55, 50, 45 or 40% of the width of the belt, from the external mechanical obstacle module. The external mechanical obstacle module(s) may be positioned adjacent the treadmill belt such that the obstacle is extendable vertically above the belt, e.g., at least 1, 2, 2.5, 5, 7.5, 10, 12.5, 15, 20, 25, or 30 cm and/or up to 100, 75, 60, 50, 40, 35, 30, 25, or 20 cm. The orientation of the obstacle(s) may be parallel planar to the plane of the belt, or skewed, and/or the orientation of the obstacle may be perpendicular to the direction of the rotation/movement of the belt, or angled, e.g., at least 3, 6, 9, 12, 15, 18, 21, 24, or 30° and/or up to 60, 57, 54, 51, 48, 45, 42, 39, 36, 33, or 30°. The obstacle may be configured to extend perpendicular to the first and second lengthwise edge of the belt. The obstacle may be configured to extend across no more than 60, 57.5, 55, 52.5, 50, 47.5, 45, 42.5, 40, 37.5, or 36.7% of the width of the belt, typically from one side of the belt, i.e., generally not simply a middle belt portion.

The external mechanical obstacle module (at least the housing) may be integral with the hollow frame. The external mechanical obstacle module may be configurable with electronic instructions to extend and retract the rod according to an exercise regimen, whereby such instructions may be transmitted internally in the external mechanical obstacle module from an electronic device on the external mechanical obstacle module, or via an external handheld, laptop, or desktop device (optionally wirelessly), or wirelessly via a central service. For example, the obstacle(s) on the external mechanical obstacle module may be programmed to extend and retract at certain intervals, e.g., at least 1 time per 60, 50, 45, 40, 35, 30, 25, 20, 15, 10, 5, 4, 3, 2, or 1 second and/or up to 1 time per 10, 9, 8, 7, 6, 5, 4.5, 4, 3.5, 3, 2.5, 2, 1.5, 1, 0.75, 0.5, 0.25 seconds. The direction of motion of the obstacle may also be programmed in a variety of ways, including to sway in a hinged manner (e.g., in a range of any combination of ±45, 42, 39, 36, 33, 30, 27, 24, 21, 18, 15, 12, 9, 6, 5, 4, 3, 2, 1° from perpendicular to the direction of movement of the belt), translating back and forth in the horizontal plane (e.g., in a range of any combination of ±100, 90, 80, 75, 70, 65, 60, 55, 50, 45, 40, 35, 30, 25, 20, 15, 10, or 5 cm), translating up and down in the vertical plane (e.g., in a range of any combination of ±100, 90, 80, 75, 70, 65, 60, 55, 50, 45, 40, 35, 30, 25, 20, 15, 10, or 5 cm), translating in a diagonal between the vertical and horizontal planes (e.g., in a range of any combination of ±45, 42, 39, 36, 33, 30, 27, 24, 21, 18, 15, 12, 9, 6, 5, 4, 3, 2, 1° off of the vertical and/or horizontal plane), and/or in a circular, ovular, FIG.-8, and/or sinusoidal manner (viewed from FIG. 8B, i.e., making such shapes in the vertical plane). Based on attachments on the obstacle(s), the shape of the obstacle(s), or mechanical motion of the external mechanical obstacle module, such shapes may also be made in the horizontal plane and/or any diagonal to the horizontal plane.

The exercise (regime) may be any known in the art and/or recommended by a qualified orthopedist, doctor (doctor of medicine, osteopathy, podiatric medicine, etc.), nurse (physician assistant, clinical nurse specialist, or nurse practitioner), and/or physical therapist. The exercise regime may be any type of gait training, for example, suitable to strengthen muscles, strengthen joints, improve balance, improve posture, build endurance, develop muscle memory, retrain legs for repetitive motion, lower risk of falls, and/or increase mobility. The training may be motivated by, e.g., one or more spinal cord injuries, broken legs/pelvis, joint injuries, joint replacements, lower limb amputations, strokes, neurological disorders, and/or muscular dystrophy or other musculoskeletal disorders.

Inventive treadmills may further comprise: a set of frame magnetic coils, e.g., 1, 2, 3, 4, 5, or more coils on the right, left, rear, front, bottom, and/or top side, configured to create an electromagnetic field barrier generated from the set of magnetic coils; and a wearable magnet magnetically coupled with the set of frame magnetic coils. Such magnet may be incorporated into a shoe and/or on a clamp/shoe jacket/saddle configured to attach onto customary non-therapeutic (or therapeutic) shoes worn by the public. The set of magnetic coils may be integrated into a treadmill frame, e.g., within 50, 47.5, 45, 42.5, 40, 37.5, 35, 32.5, 30, 27.5, 25, 22.5, 20 cm (vertically) of the base or belt. The wearable magnet may be configured to be integrated into or onto a shoe worn by the person on the treadmill, and the set of frame magnetic coils and the at least one wearable magnet may be operatively coupled with a microprocessor, such that electromagnetic signals and impulses may be sent from or received by the coils and/or the wearable magnet.

Inventive treadmills may further comprise: a foot sensor; a front stride sensor; and/or a rear stride sensor, which may be independently in the form of single plate sensors or arrays of sensors. The foot sensor may be configured to be integrated into a shoe or some form of attachment for the shoe worn by the person on the treadmill. The foot sensor may be communicably coupled (e.g., electromagnetically, typically by wireless signal) with the front stride sensor and the rear stride sensor, though systems may be used in which piezoelectric sensors require no foot sensor. The foot sensor, the front stride sensor, and/or the rear stride sensor, typically each sensor independently, may be operatively coupled with a microprocessor, a set of strike related information being transferred to the microprocessor from the sensors, and the electromagnetic field is managed by the microprocessor according to the set of strike related information. This system can be coordinated and/or integrated with the magnetic coils and/or wearable magnet, or may be independently operated with an electronically responsive element on the foot, ankle, calf, and/or knee. Such pulses may be implemented to torsionally rotate and/or linearly translate the foot, ankle, calf, and/or knee, e.g., to thereby correct, modify, improve, etc., ambulatory motion.

The first and second barrier may include a first belt side attachment and a second belt side attachment (or further attachments), which may be connected in a bearing system to the belt, e.g., with a spherical, ovular, cylindrical, etc., barrier element to a front (e.g., toe and/or ball of foot) and/or back (heel and/or back arch) of a person's foot or shoe. The treadmill may further comprise a lengthwise treadmill wall positioned along the first lengthwise edge; and a center treadmill wall positioned parallel to the lengthwise treadmill wall and along a center of the treadmill belt. Such walls may be present without affecting the integrity of the belt, e.g., in that the center wall hovers over a single, integral belt. The first belt side attachment may be laterally connected to a shoe worn by the person on the treadmill, and the second belt side attachment may be laterally connected to the shoe opposite the first lateral attachment, e.g., based on a physical (cable) connection or signal connection between the barrier element and the shoe from the center wall and side wall. The first belt side attachment may be slidably positioned along the lengthwise treadmill wall using a first rotatable ball (or oval, cylinder, or other rotatable) mount. The second belt side attachment is slidably positioned along the center treadmill wall using a second rotatable ball mount (or oval, cylinder, or other rotatable). The first and second rotatable ball mount may be identical in shape, but may preferably be different, e.g., providing more or less pressure to one end of the foot, based upon the needs and/or goals of the person on the treadmill.

The first and second barrier may be in the form of triangular and/or rectangular prisms (or other shape described below). The width of the barrier may be, e.g., at least 15, 20, 25, 30, or 33% of the width of the belt and/or up to 50, 47.5, 45, 42.5, 40, 37.5, 35, 32.5, or 30% of the width of the belt, and/or the thickness (depth) of the barrier may be, e.g., at least 2.5, 5, 7.5, or 10 cm and/or up to 25, 22.5, 20, 17.5, 15, 12.5, 10, 7.5, or 5 cm. The belt may comprise the barriers on only one half of the width of the belt from a center of the belt, i.e., on the right or left side. The barriers may be driven only by the belt in operation, i.e., the only element of the treadmill causing the barriers to move may be the belt itself and the static connection of the barrier to the belt, rather than a further driving system to the belt/rotating elements. Each of the barriers may be mirror-symmetric in at least two planes bisecting the barrier, such as a rectangular prism, isosceles triangular prism, trapezoidal prism, or the like. The barriers may be made of a material comprising a polyurethane (PU) foam (incl. low-resilience PU, memory foam), or a similar polymer foam or rubber, e.g., olefinic (LDPE, PE, PP, expanded PP, etc.) foam, polyethylene-vinyl acetate (PEVA), nitrile rubber (NBR)

foam, acrylonitrile (ACN)-butadiene copolymer foams, polychloroprene foam, polyimide foam, polypropylene paper (PPP), polystyrene (PS or expanded PS or extruded PS) foam, polyvinyl chloride (PVC or closed-cell PVC) foam, silicone foam, SBR, butadiene, ABS, etc. The barriers may also be harder materials, such as wood, aluminum, steel, titanium, or the like, but may preferably be softer than wood and/or structural metal.

Aspects of the invention provide methods of correcting a gait of a person, and such methods may comprise: conducting a physical therapy regime on ambulatory motion of the person using any permutation of the inventive treadmill described herein. The physical therapy may be a part of regular sessions, wherein the method of correction is regularly changed, e.g., increased in stress, and may occur daily or weekly (e.g., 1, 2, 3, 4, or 5 times) and may take place over, e.g., at least 15, 20, 25, 30, 45, or 60 minutes and/or up to 3, 2.5, 2, 1.5, 1, 0.75, or 0.5 hours per session. The therapies may last over 1, 2, 3, 4, 6, 8, 10, or 12 weeks, or may be chronic over similar numbers of months or years.

Aspects of the invention provide methods of conducting physical therapy on the gait of a person, and such methods may comprise: aligning the barriers of any permutation of the inventive treadmill described herein on only one lengthwise half of the belt in the direction of movement of the belt; and allowing the person to walk and/or run on the treadmill.

Inventive arrangements may function fully without harnesses, cables, sensors, or the like contacting or attached to the patient. Inventive arrangements may function fully without force transducers, winches, and/or weighting in communication, particularly cable communication, with the treadmill, patient, and/or belt. Inventive arranges generally create disturbance events in greater than 500 ms, e.g., at least 0.5, 0.6, 0.75, 1, 1.25, 1.5, 1.75, or 2 s and/or up to 10, 9, 8, 7, 6, 5, 4, 3, 2, or 1 s.

Inventive arrangements may be configured to have no implements, braces, brackets, harnesses, belts, etc., above the leg(s) of the person on the treadmill, i.e., a waist-upwards free mechanism (uncontacted by elements of the treadmill system).

Aspects of the invention comprise minimizing the asymmetry of the step length and/or time on the least affected limb without adding extra weight and/or accessories to the patients. Aspects of the invention include a mechanical device and/or detachable barriers attached to a treadmill with a special belt, which may function as an obstacle to reduce the speed of the sound limb, thus minimizing the walking asymmetry.

Aspects of the invention provide methods and/or devices configured to activate gait symmetry, efficiency, and/or speed in patients (e.g., humans, canines, equines, etc.) with asymmetrical gait disorders. Aspects of the invention include methods and/or devices configured to improve the strength of affected lower limb(s). Aspects of the invention provide methods and/or devices configured to reduce the incidence of tripping and falling in users of such methods and/or devices. Aspects of the invention comprise methods and/or devices configured to minimize secondary postural deviations in users of such methods and/or devices. Aspects of the invention provide methods and/or devices configured to improve body image and body scheme in users of such methods and/or devices. Aspects of the invention include methods and/or devices configured to enhance dual task cognitive skills in users of such methods and/or devices.

Referring now to the drawings, wherein like reference numerals designate identical or corresponding parts throughout the several views.

FIG. 1 shows an exemplary treadmill equipped with an exemplary specialized belt. The walking belt in FIG. 1 includes holders (1), e.g., hooks, clamps, fixation elements, holes, or any similar fixation element known in the art, configured for the (preferably removable) attachment of a barrier (2)/obstacle to the walking belt (3) that can be used, e.g., to slow down of the healthy leg or to urge forward, motivate movement, etc. of the unhealthy or healthy leg. While the barrier (2) is illustrated as (isosceles) triangular prismatic elements, any morphology suitable to achieve a desired therapeutic or motor-skill exercise may be used, including right triangular prismatic, square prismatic, rectangular prismatic, (hemi)spherical, cylindrical, half-pipe shaped, half hexagonal prismatic, half octagonal prismatic, saw-toothed (seen from above), sinusoidal (seen from above), squared stepped (seen from above), circular (seen from above), half-circular (seen from above), horse-shoed (seen from above), V-shaped (seen from above), L-shaped (seen from above), etc. The holder (1) may be any customary fixation element(s) known in the art, including holes, Velcro, hooks, rivets, buttons, zippers, clasps, clamps, flanges, snap-ons, loops, etc., as female or male or mixed topography.

FIG. 2A to 2D show top (FIG. 2A), rear (FIG. 2B), side (FIG. 2C), and front (FIG. 2C) views of an exemplary treadmill and an exemplary specialized belt (3). The belt (3) may have holders (1) that can be of different varieties, shapes, or implementations, as discussed above. The holders (1) are generally configured to hold walking barriers (2). The barriers can be positioned either on the left or the right side depending on which leg is being targeted, and may be oriented to have an elongated side in the direction of rotation of the belt (3) and/or perpendicular to the direction of rotation of the belt (3).

A conventional treadmill, like inventive belts, may have a running belt (3) that rotates around one or more rollers having axes oriented perpendicularly to the direction of rotation. The speed of the rotation (or translation of the belt, 3) can be adjusted so that the user can experience a full spectrum of speeds from walk to sprint. Unlike conventional treadmills, inventive treadmills may be equipped with a specialized belts (3) fitted with and/or configured for adjustable and/or removable obstacles or barriers (2). The net effect of such inventive devices may be a negative influence on the speed of one leg (limb) over the other.

Figure 3:
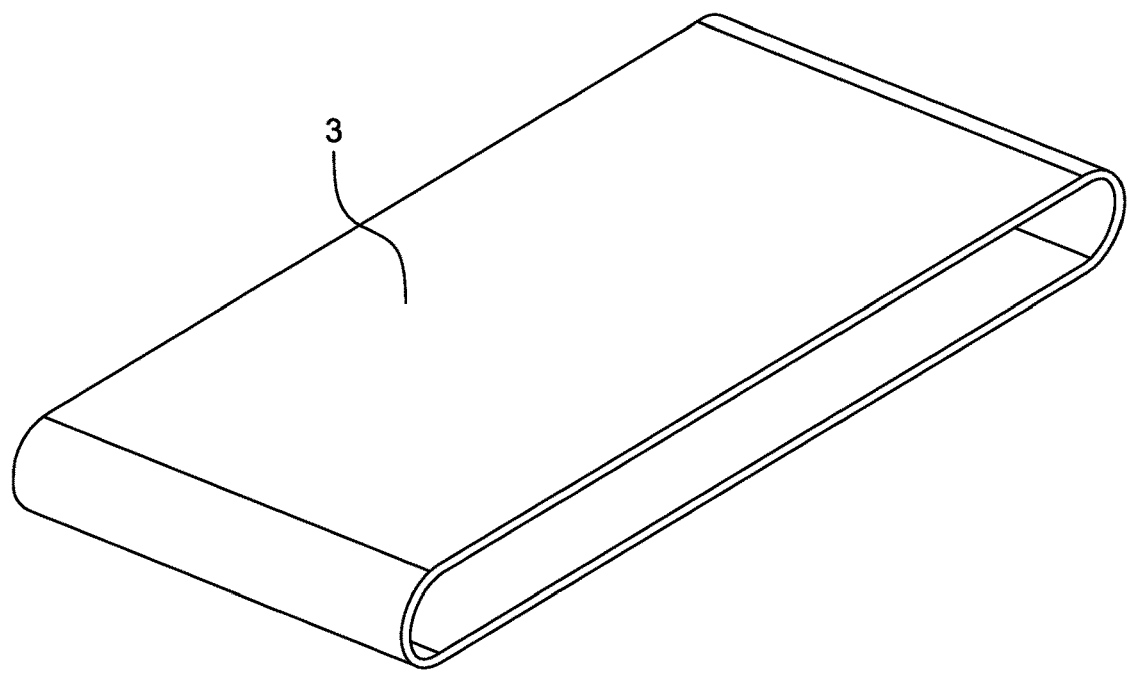
FIG. 3 shows an exemplary treadmill belt useful within the scope of the invention.

FIG. 3 shows a specialized treadmill belt (3) within the scope of the invention, which does not show any attached barriers (2). The specialized belt is generally modified with holders (1), such as fitting holes or Velcro tape or any other type of fitting element which can hold or host barriers (2)/obstacles (21). Such modified belts (3) may then be added to a treadmill on which a walking impaired person enters or is placed. As the belt (3) moves the person may need to raise his/her non-effected leg in order to slow down, which should ensure that the affected leg and non-affected leg move at the same speed. The belt (3) may be designed to fit as many obstacles as needed, e.g., at least 1 per 30, 35, 40, 45, 50, 55, 60, 65,70, 75, 80, 90, 100, 125, 133, 150, 167, 175, 200, 250, 300 cm, or more and/or up to 1 per 10, 15, 20, 25, 30, 33, 35, 40, 45, 50, 60, 75, or 100 cm. The belt (3) may contain 1, 2, 3, 4, or 5 barriers, depending upon the shape, across its width, and/or may contain staggered barriers (2)/obstacles (21) across its width and length. The barriers (2)/obstacles (21) may be arranged on only one side or both sides, vis-à-vis the legs of the subject.

Figure 4:
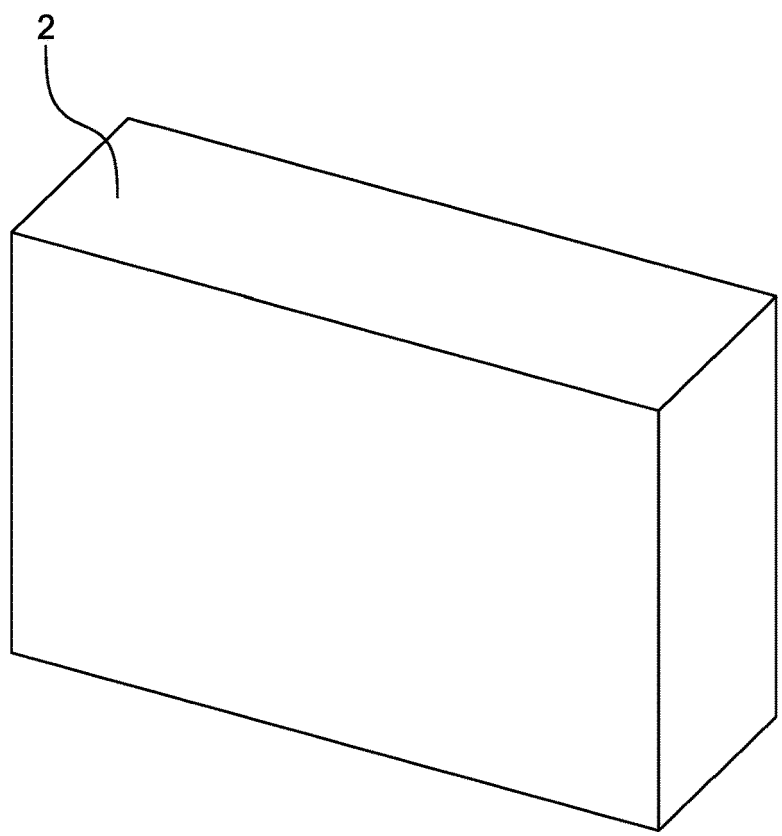
FIG. 4 shows an exemplary purposefully-made obstacle useful within the scope of the invention.

FIG. 4 shows an exemplary purposively made barrier (2)/obstacle (21). Useful barriers (2)/obstacles (21) may be configured or manufactured such that the barriers (2)/obstacles (21) can be fitted onto specialized belt(s) (3). The barriers (2)/obstacles (21) may be added/arranged or removed, e.g., attached or detached, as needed to achieve an overall goal. The obstacles barriers (2)/obstacles (21) may have on a bottom side some affixation elements, such as pins, Velcro, carabiners, snap-ons, or the like, to attach the barriers (2)/obstacles (21) to the treadmill belt (3). Useful barriers (2)/obstacles (21) may have various heights and depths, e.g., at least 1, 1.5, 2, 2.5, 3, 3.5, 4, 5, 6, 7.5, or 10 cm and/or up to 30, 25, 20, 17.5, 15, 12.5, 10, 9, 8, 7, 6, or 5 cm in height and/or width, and each barrier (2)/obstacle (21) may be different from other barriers (2)/obstacles (21) on the same belt (3) or patterns of barriers (2)/obstacles (21) may exist on a single belt (3). Thus, based on the needs and progression of the treatment of the patients, the physician will have in his/her disposal different barriers (2)/obstacles (21) to advance the treatment or achieve a training goal.

Figure 5:
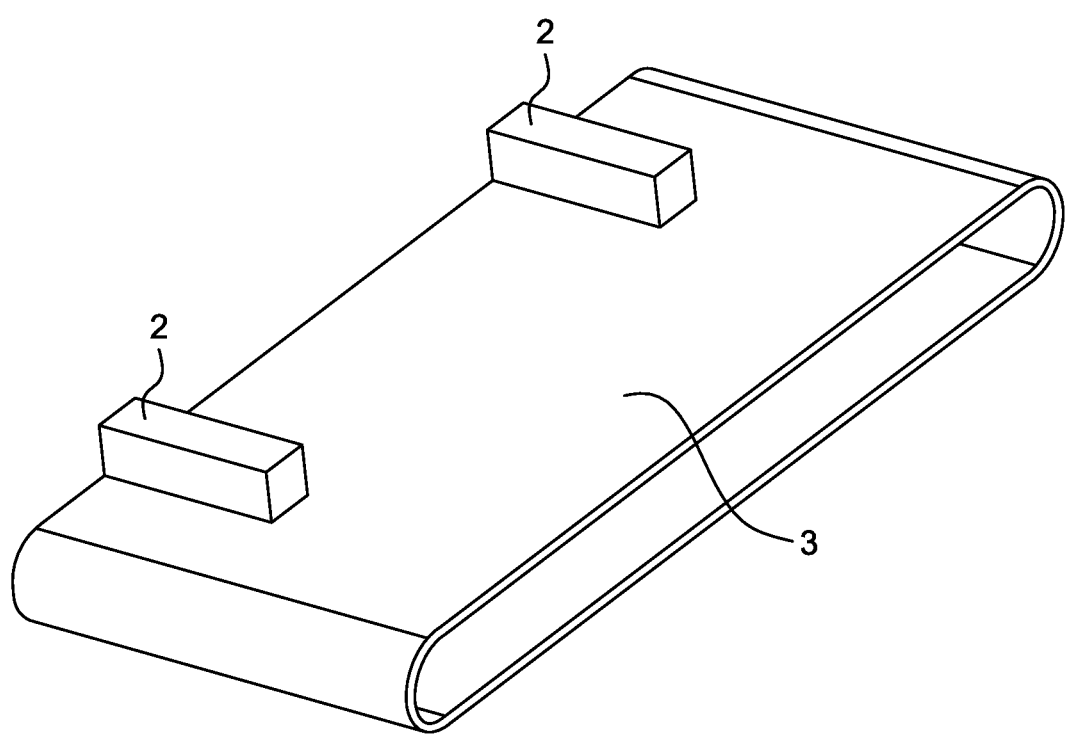
FIG. 5 shows an exemplary specialized belt equipped with walking obstacles useful within the scope of the invention.

FIG. 5 shows an exemplary specialized belt (3) equipped with exemplary barriers (2)/obstacles (21). The specialized belt (3) and barriers (2)/obstacles (21) may together provide a device capable of adjusting the walking speed of the non-affected leg to match the speed of the affected leg, or vice-versa. FIG. 5 merely shows a simple arrangement within the scope of the invention, though the belt (3) may have offset (width-wise) barriers (2) and/or barriers (2) of different shape and/or barriers (2) of varied, i.e., non-uniform, length-wise distribution along the rotational direction of the belt (3).

Figure 6:
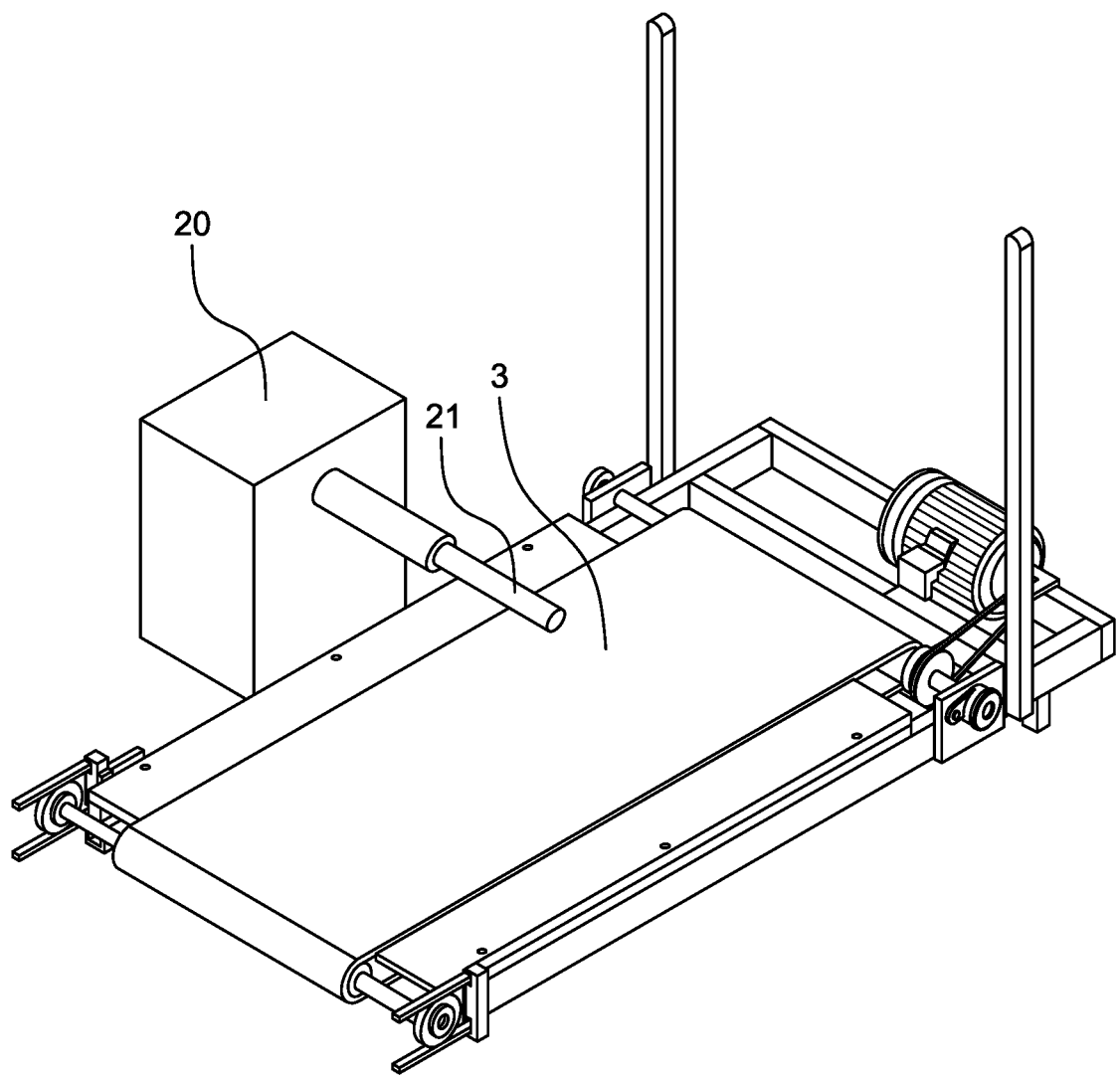
FIG. 6 shows an exemplary treadmill with an exemplary mechanical obstacle module which may be programmed to trigger with healthy leg motion.

FIG. 6 shows an exemplary treadmill with mechanical obstacle module (20) in a triggered arrangement, e.g., for training healthy leg motion, though the belt (3) does not specifically show any further barriers (2), which may be present. As desired for the particular therapy or training regiment, a box (20), or other housing or retractable arm from, e.g., the base of the treadmill, may be included in the treadmill. Such a box may have one, two, three, or more mechanical rods that is extendable and retractable, either telescopically, rotationally, foldingly, or otherwise. While the depictions in the drawings show only a vertical translation, such obstacles (21) may be radially rotated, like a baseball bat, and/or translated back and forth in the direction of the rotation of the belt (3), and/or may have a circular, sinusoidal, "FIG. 8," etc., motion pattern.

A conventional treadmill, like inventive treadmills, may have a running belt (3) that moves around the base with a top surface and a bottom surface in an infinite loop. The speed of the movement of the belt (3) may be adjusted so that the user can experience any value within a full spectrum continuum of speeds from walk to sprint, e.g., at least 0.1, 0.25, 0.5, 0.75, 1, 1.5, 2, 2.5, 3, 3.5, 4, 4.5, or 5 km/h and/or up to 30, 27.5, 25, 22.5, 20, 18, 16, 15, 14, 13, 12, 11, 10, 9, 8, 7, 6, or 5 km/h. Unlike conventional treadmills, inventive arrangements may have 1, 2, 3, 4, or more mechanical obstacle modules (20), e.g., with one or more extendable and retractable rods as obstacles (21). The housing for such a mechanical obstacle module (20) may be placed on either side, both sides, or pluralities thereof, of the treadmill and the obstacles (3) may extend a quarter, one-third, halfway, or more, over the belt (3) or walking area. In such an operation, one leg may be unaffected by the rod while the other leg may have an obstacle (21) to move over. Such obstacles (21) may be, for example, at least 5, 10, 15, 20, 25, 30, 35, 40, 45, or 50 cm and/or up to 100, 75, 65, 60, 55, 50, 45, 40, 35, 30, 25, or 20 cm high. The mechanical obstacle modules (20) will generally work together with the treadmill. As the user moves his foot (12, 13) forward, the rod/obstacle (21) may extend, causing the user to need to move his foot (12, 13) over the rod/obstacle (21) thus adding time to the stride and effectively slowing it down. Once the leg has landed on the other side of the rod/obstacle (21), the rod/obstacle (21) may retract so that the user can move his leg back in a normal way. If the speed of the treadmill is adjusted, the frequency with which the obstacle (21) extends and retracts may also be adjusted.

One or more shapes or obstacles may be mounted on the distal end of the retractable rod (21) to act as an obstacle. The shape is preferably structured to require a patient to lift a leg over an obstacle in the direction of travel of the belt (3). The shaped obstacle they have different or varying dimensions with respect to its vertical placement from the plane of the moving belt (3). For example, an obstacle such as a long rectangle having a plane that is substantially parallel to the plane of the moving belt (3) can be mounted on the rod (21). An obstacle in this form is intended to mimic or represent a longer obstacle that might normally be encountered while walking such as a larger crevice, curb, or step.

Figure 7:
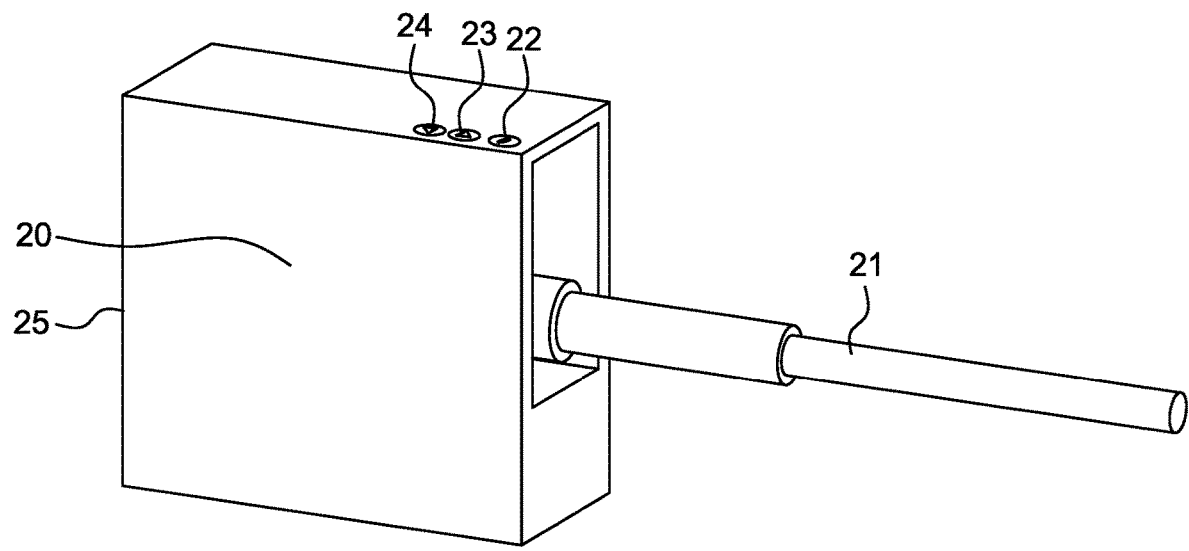
FIG. 7 shows the exemplary mechanical obstacle module from FIG. 6.

FIG. 7 shows an isolated view of an exemplary mechanical obstacle system (20) of the sort shown in FIG. 6. In FIG. 7, the mechanical rod obstacle (21) may extend in front of the healthy leg to slow down the gait. Such obstacles (21) can be adjusted upwards and downwards and/or otherwise as described above. Typically, the higher the rod goes, the slower the gait will be. One or more sensors to detect the starting of motion for a leg can be added to trigger the release of the rod/obstacle (21) with the starting of motion.

Figure 8A:
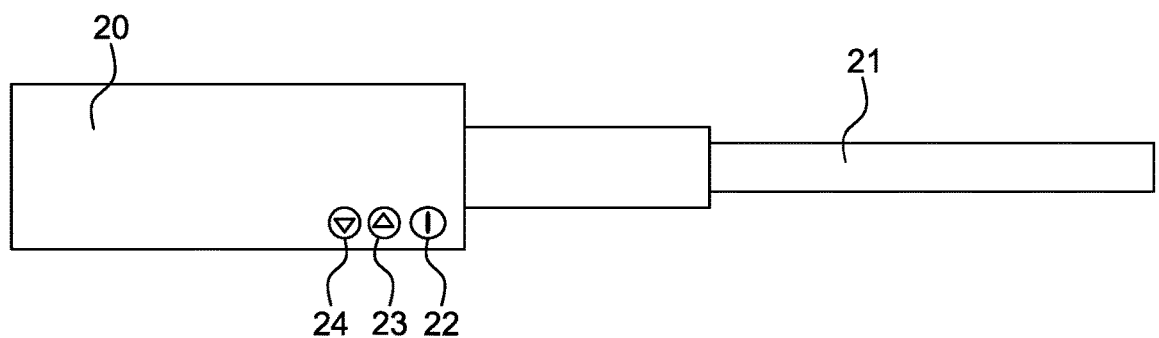
FIG. 8A shows a top plan view of components of the exemplary mechanical obstacle module from FIG. 6.
Figure 8B:
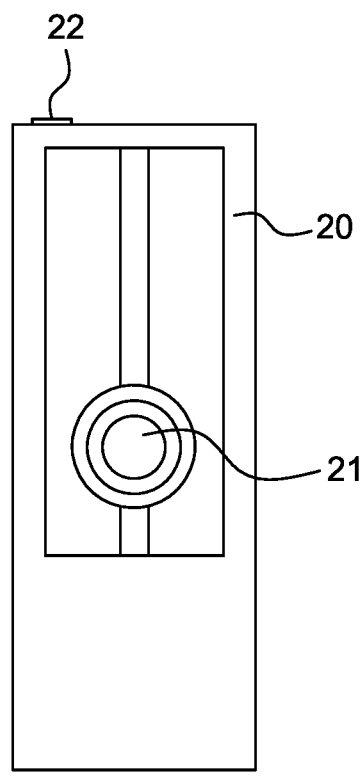
FIG. 8B shows a (right) side view of components of the exemplary mechanical obstacle module from FIG. 6.
Figure 8C:
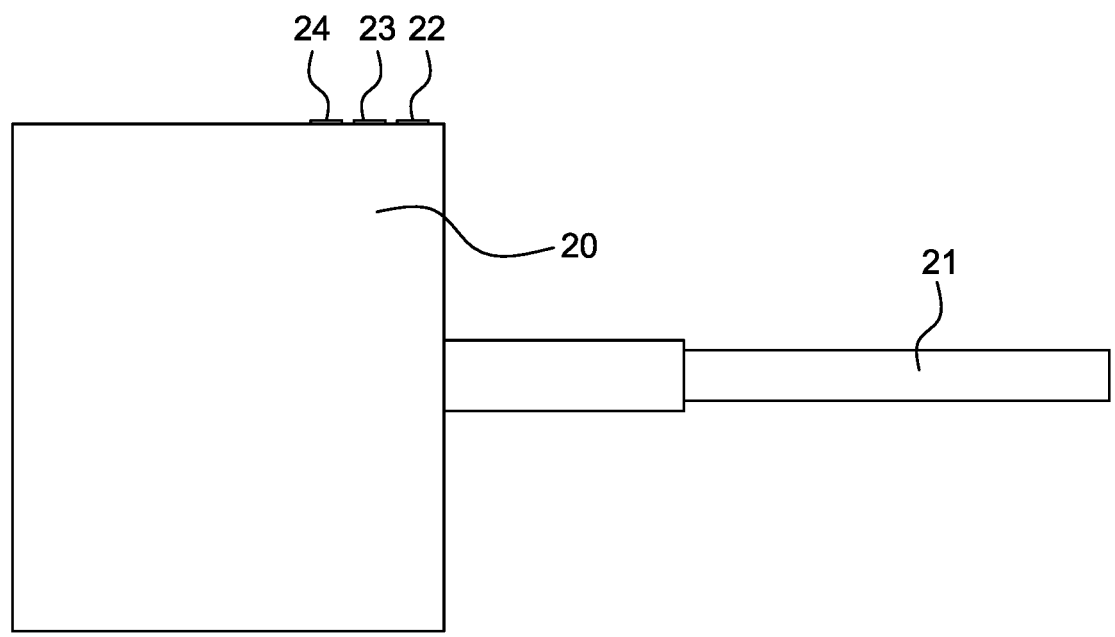
FIG. 8C shows a rear view of components of the exemplary mechanical obstacle module from FIG. 6.
Figure 8D:
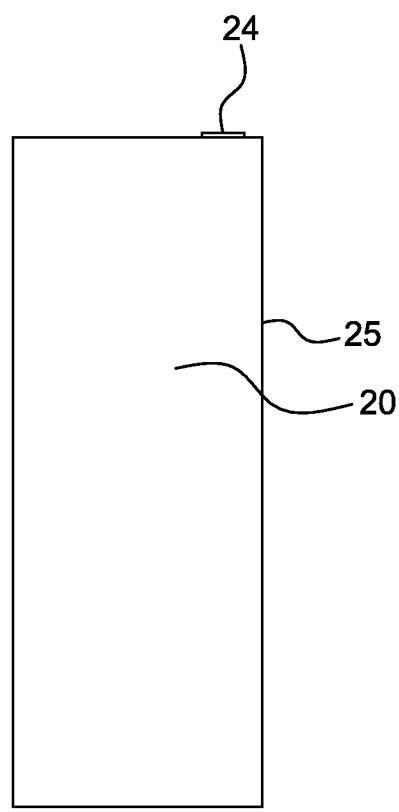
FIG. 8D shows a (left) side view of components of the exemplary mechanical obstacle module from FIG. 6.

FIG. 8A to 8D shows components of an exemplary mechanical obstacle system (21) that may be included in a device as desired. Of course, the electrical controller (25) may include a receiver for electronic signals from a hand-held device, remote control, computer, or the like, for controlling and/or influencing the motion of the treadmill, belt (3), and/or the mechanical obstacle system (21). Any mechanical obstacle system (21) and/or barriers (2) on the belt (3) may have programmable patterns of motion. Although the location of the buttons may be any desired (or none, or a touch-screen), FIG. 8A shows an on/off button (22), a button (23) to move an obstacle (21) vertically upwards, a button (24) to move an obstacle (21) vertically downwards, and at least one electric controller (25) which may be within a housing (21) as shown, or within the obstacle (21) itself or within the standard front display of the treadmill.

Figure 9:
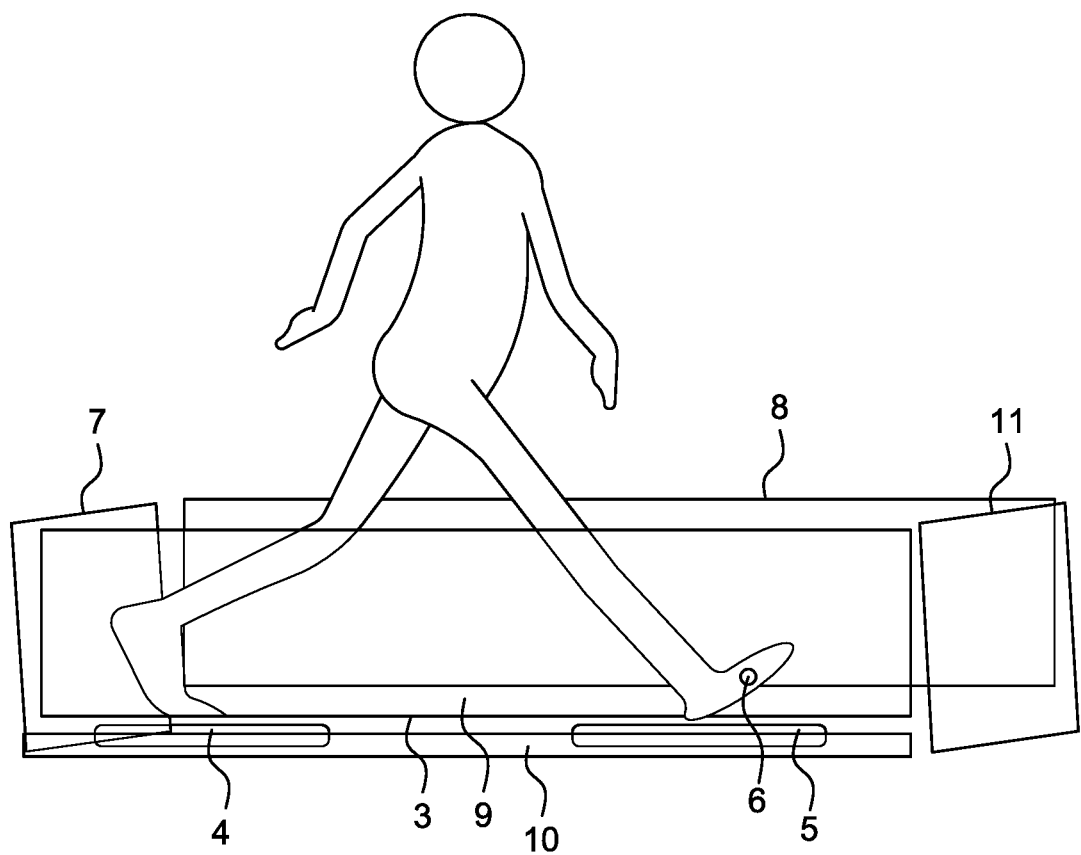
FIG. 9 shows exemplary electromagnetic shoes, sensors, coil zones, and a corresponding treadmill track.

FIG. 9 shows an exemplary electromagnetic shoe including an intended foot indicator (6) and an exemplary treadmill track including a belt (3), one or more sensors (4, 5), and/or one or more coils (7, 8, 9, 10, 11) optionally suitable for detecting movements of any electronic device, e.g., attached to the shoe, foot, ankle, calf, knee, and/or thigh of a patient.

Figure 10:
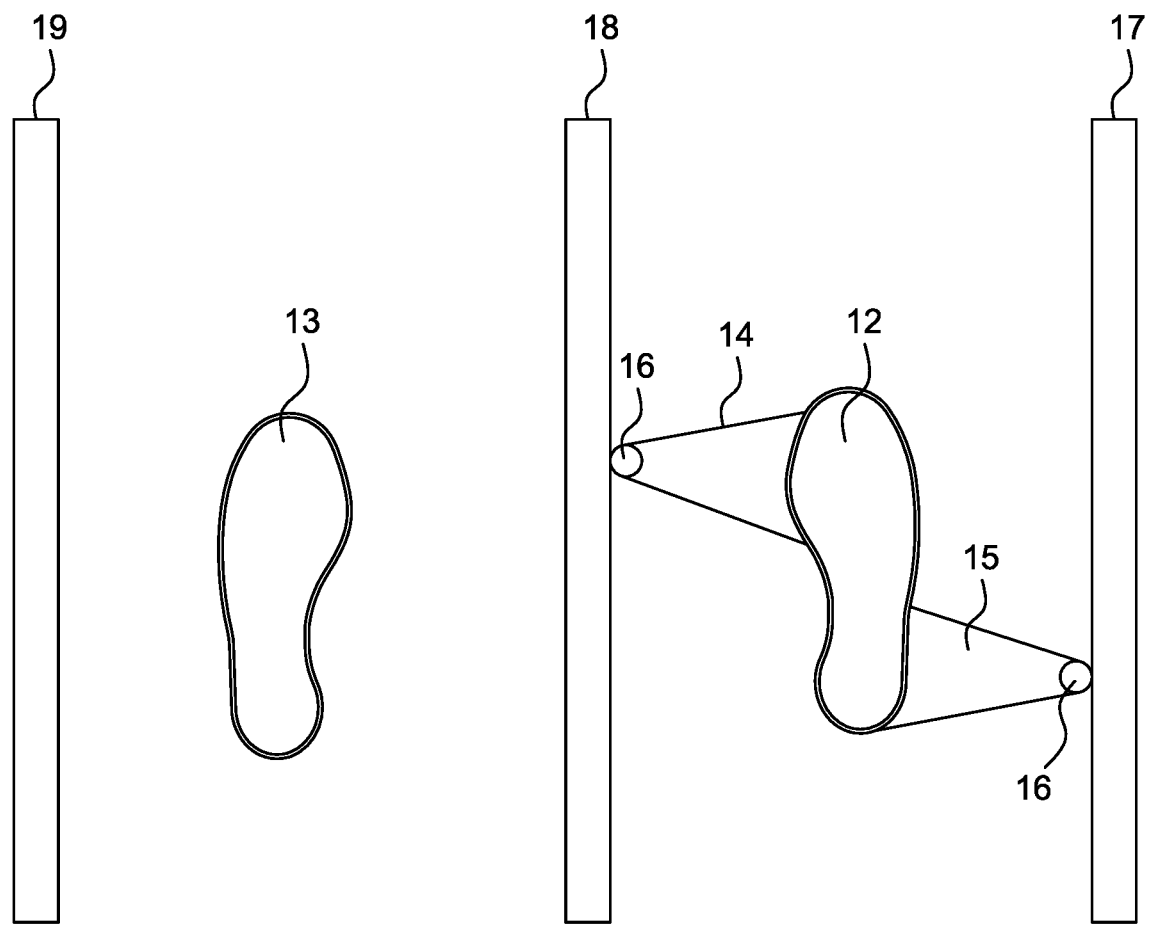
FIG. 10 shows a top plan view of an illustration of a method of function of a heal-toe barrier/sensor arrangement as disclosed in FIG. 9.

FIG. 10 shows a layout of an exemplary walking system, showing an image of a right shoe/foot (12), a left shoe/foot (13), a front spacer (14) and a rear spacer (15), one or more rotating balls/spheres (16), cylinders, or the like, e.g., having 360° in one, two, or three axes. Also shown on the exemplary layout in FIG. 10 are a right treadmill wall (17), a center treadmill wall (18), and a left treadmill wall (19), any of which may be present or absent.

In the depiction in FIGS. 9 and 10, the right leg has the unhealthy foot (12) and the left foot (13) is healthy. The situation of the feet shown in FIGS. 9 or 10 can be reversed and/or both feet (12, 13) may include attachments (6). The shoe sides and the sole can be made from or laced with small magnets, piezoelectrics, and/or signal elements. The sides, front, back, and/or bottom of the treadmill may include one or more magnetic coils (7, 8, 9, 10, 11) which may generate an electromagnetic signal, or in which an electromagnetic signal may be developed, as shown in FIG. 9. The strength and/or direction of the fields may be adjusted physically and/or electronically: physically e.g., by configuring the orientation, the winding geometry, the coil material/alloy, and/or the number of turns of the coil; and electronically, through a microprocessor (unnumbered) which may control the energizing timing of the coil (7, 8, 9, 10, 11) shown in FIG. 9 and/or the strength and direction of the current and voltage energizing the coils.

The shoe and/or the foot (12, 13) may have an indicator (6) on the foot of one or both legs. The indicator (6) may be infrared, light reflector, or any other suitable indicator. The magnets in the shoe (12, 13) or otherwise arranged on the foot (12, 13) can also act as the indicator (1). The treadmill may have 1, 2, 3, 4, 5, 6, or more sensors (7, 8, 9, 10, 11), such as one or more in the front, rear, right side, left side, and/or bottom, as seen in FIG. 10. In this way, one or more sensors (7, 8, 9, 10, 11) may determine the beginning and end of each stride on the desired foot (12, 13) and relay this information to a microprocessor suitable to adjust the electromagnetic field accordingly to either oppose or assist the shoe movement. The adjustment may thus achieve a desired modification of the gait behavior of the healthy and/or impaired legs.

The magnetic field shape may additionally or alternatively be adjusted dynamically during the gait to force and adjust the orientation and posture of the foot (12, 13), thus training the user to move the foot (12, 13) in the correct direction and/or at the correct pace. For example, the user may have the front of his right foot (12) rotated counterclockwise, i.e., having toes of the right feet point inwards towards the left foot, while the heel of the right foot (12) is pointed outwards (or the reverse of this, i.e., clockwise rotated). In the counter-clockwise case, a magnetic field may be used to force the right foot (12) to rotate clockwise during the gait.

FIG. 10 shows exemplary sides (17, 18, 19) of an exemplary treadmill, wherein the center (18) may have a wall of any desired height, e.g., at least 1, 2.5, 5, 7.5, 10, 12, 15, 20, 25, or 30 cm and/or up to 75, 70, 65, 60, 55, 50, 45, 40, 35, 30, or 25 cm. The shoe (12, 13) may include 1, 2, 3, 4, 5, or more attachments (6, 16) having shapes customized for each patient to achieve the desired foot orientation and can be fitted to any side of the foot (12, 13) in the front, right side, left side, top, sole, and/or back, and/or standardized to typical impairment scenarios encountered across particular patient groups. The outer edge of such attachments (6, 16) may include a ball (16) that can rotate freely in 360 degrees to thereby allow a customization of the shape, length, and/or width of these attachments to orient the foot (12, 13) in a desired direction. Such balls (16) may be in contact with the treadmill walls (17, 18, 19) so the foot (12, 13) can be oriented in the desired health direction. The attachments (6, 16) may be adjusted gradually so as to train a user over time, making bigger and bigger changes until the final desired outcome is achieved. In FIG. 10, it is assumed that the right leg has the impaired/unhealthy foot (12), and the left foot (13) is healthy/normal. However, this can be switched or even attachments (6, 16) can be attached to both feet (12, 13).

Numerous modifications and variations of the present invention are possible in light of the above teachings. It is therefore to be understood that within the scope of the appended claims, the invention may be practiced otherwise than as specifically described herein.

REFERENCE SIGNS 1 holder/mount
2 barrier
3 treadmill surface
4 rear (stride) sensor
5 front (stride) sensor
6 intended foot indicator
7 rear coil
8 right side coil
9 left side coil
10 bottom coil
11 front coil
12 right shoe/foot
13 left shoe/foot
14 front spacer
15 rear spacer
16 (360° rotating ball
17 right treadmill wall
18 center treadmill wall
19 left treadmill wall
20 mechanical obstacle system
21 obstacle
22 on/off button
23 move obstacle vertically up
24 move obstacle vertically down
25 electric controller

The invention claimed is:

1. An apparatus for human gait manipulation, comprising:
a treadmill belt configured to travel within a hollow treadmill frame upon rotating elements having axes perpendicular to a direction of the travel;
a first barrier; and
a second barrier,
a third barrier, and
an external mechanical obstacle module comprising an extendable/retractable rod-shaped obstacle,
wherein the first, second and third barriers are equidistantly positioned along a length of the treadmill belt
wherein the extendable/retractable rod-shaped obstacle is configured to extend lengthwise perpendicular to a first and second lengthwise edge of the treadmill belt across no more than 60% of the width of the treadmill belt of the apparatus from the external mechanical obstacle module,
wherein the first, second and third barriers are arranged on the top surface of the treadmill belt between the first lengthwise edge and the second lengthwise edge of the treadmill belt,
wherein the first, second and third barriers are reversibly fastened to the treadmill belt and are interchangeably positionable along the first lengthwise edge and the second lengthwise edge of the treadmill belt,
wherein the first, second and third barriers extend no more than 75% of a width between the first and second lengthwise edge,
wherein the first, second and third barriers on the treadmill belt are configured to modify movement of only one foot of a person on the apparatus, and
wherein a distance between the first lengthwise edge and the second lengthwise edge of the treadmill belt defines the width of the treadmill belt.

2. The apparatus of claim 1, configured to have no physical connection between the person on the apparatus and the hollow treadmill frame.

3. The apparatus of claim 1, wherein the external mechanical obstacle module is positioned adjacent the treadmill belt such that the extendable/retractable rod-shaped obstacle is extendable vertically above the treadmill belt.

4. The apparatus of claim 1, wherein the first, second and third barrier are in the form of triangular and/or rectangular prisms.

5. The apparatus of claim 1, wherein the treadmill belt comprises the first, second and third barriers on only one half of the width of the treadmill belt from a center of the treadmill belt.

6. The apparatus of claim 1, wherein the first, second and third barriers are driven only by the treadmill belt in operation.

7. The apparatus of claim 1, wherein each of the first, second and third barriers is mirror-symmetric in at least two planes bisecting the respective barrier.

8. The apparatus of claim 1, wherein the first, second and third barriers are made of a material comprising a polyurethane foam.

* * * * *